US010040869B2

(12) United States Patent
Nur et al.

(10) Patent No.: US 10,040,869 B2
(45) Date of Patent: Aug. 7, 2018

(54) MOLECULES MIMICKING AN AUTOANTIBODY IDIOTYPE AND COMPOSITIONS CONTAINING SAME

(71) Applicant: Omrix Biopharmaceuticals Inc., Somerville, NJ (US)

(72) Inventors: Israel Nur, Moshav Timurim (IL); Yehuda Shoenfeld, Ramat Gan (IL); Miri Blank, Tel Aviv (IL)

(73) Assignee: OMRIX BIOPHARMACEUTICALS LTD., Rehovot (IL)

( * ) Notice: Subject to any disclaimer, the term of this patent is extended or adjusted under 35 U.S.C. 154(b) by 0 days.

(21) Appl. No.: 13/902,836

(22) Filed: May 26, 2013

(65) Prior Publication Data

US 2013/0244925 A1    Sep. 19, 2013

Related U.S. Application Data

(62) Division of application No. 10/515,499, filed as application No. PCT/IL03/00424 on May 22, 2002, now Pat. No. 8,450,067.

(60) Provisional application No. 60/383,136, filed on May 28, 2002.

(51) Int. Cl.
| | | |
|---|---|---|
| *A61K 38/00* | (2006.01) |
| *A61K 38/04* | (2006.01) |
| *A61K 39/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 16/42* | (2006.01) |
| *A61K 38/06* | (2006.01) |
| *A61K 38/12* | (2006.01) |
| *C07K 7/06* | (2006.01) |
| *C07K 16/06* | (2006.01) |
| *C07K 16/18* | (2006.01) |
| *C40B 30/04* | (2006.01) |
| *G01N 33/564* | (2006.01) |
| *G01N 33/68* | (2006.01) |

(52) U.S. Cl.
CPC .......... *C07K 16/4241* (2013.01); *A61K 38/06* (2013.01); *A61K 38/12* (2013.01); *C07K 7/06* (2013.01); *C07K 16/065* (2013.01); *C07K 16/18* (2013.01); *C40B 30/04* (2013.01); *G01N 33/564* (2013.01); *G01N 33/686* (2013.01); *A61K 39/00* (2013.01); *C07K 2317/565* (2013.01); *G01N 2500/04* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 4,690,905 A | 9/1987 | Diamond | |
| 5,068,177 A | 11/1991 | Carson et al. | |
| 5,882,879 A * | 3/1999 | Veenstra et al. | 435/43 |
| 6,183,997 B1 * | 2/2001 | Hogrefe | 435/91.2 |
| 6,231,856 B1 | 5/2001 | Williams | |
| 6,270,771 B1 * | 8/2001 | Guerin-Marchand et al. | 424/191.1 |
| 6,353,151 B1 * | 3/2002 | Leinwand et al. | 800/18 |
| 6,551,795 B1 * | 4/2003 | Rubenfield et al. | 435/69.1 |
| 6,864,060 B1 * | 3/2005 | Fowlkes | C07K 14/395 435/254.2 |
| 7,041,490 B1 * | 5/2006 | Griffais et al. | 435/252.3 |
| 7,067,626 B2 | 6/2006 | Benjamin et al. | |
| 7,214,786 B2 * | 5/2007 | Kovalic et al. | 536/23.6 |
| 7,504,490 B1 * | 3/2009 | Weinstock et al. | 536/23.1 |
| 2002/1058285 | 5/2001 | Kaufman | |
| 2003/0108888 A1 * | 6/2003 | Scanlan et al. | 435/6 |
| 2004/0034888 A1 * | 2/2004 | Liu et al. | 800/289 |
| 2005/0037969 A1 * | 2/2005 | Lu et al. | 514/12 |
| 2007/0009916 A1 * | 1/2007 | Suwa et al. | 435/6 |
| 2008/0229439 A1 * | 9/2008 | La Rosa | C07K 14/415 800/260 |

FOREIGN PATENT DOCUMENTS

| | | | | |
|---|---|---|---|---|
| WO | 85/102909 A1 | | 7/1985 | |
| WO | WO 1992/13884 | * | 8/1992 | .......... A61K 38/015 |
| WO | 96/30057 A1 | | 10/1996 | |
| WO | 98/26086 A1 | | 6/1998 | |
| WO | WO 2000/69898 | * | 11/2000 | ............. C07K 14/00 |
| WO | WO 2001/23429 | * | 4/2001 | .......... C07K 14/725 |
| WO | 01/49710 A2 | | 7/2001 | |
| WO | WO 2001/64835 | * | 9/2001 | |
| WO | WO 2001/81581 | * | 11/2001 | ............. C12N 15/31 |
| WO | WO 2002/34771 | * | 2/2002 | .......... C07K 14/315 |
| WO | 02/032375 A3 | | 4/2002 | |
| WO | 02/133042 A2 | | 4/2002 | |
| WO | WO 2002/079449 | * | 10/2002 | |

OTHER PUBLICATIONS

Dambaugh et al. 'U2 region of Epstein-Barr virus DNA may encode Epstein-Barr nuclear antigen 2.' PNAS. 81:7632-7636, 1984.*
Deckert et al. 'The complete genome of the hyperthermophilic bacterium Aquifex aeolicus.' Nature. 392:353-358, 1998.*
Scott et al. 'Structural requirements for the biosynthesis of backbone cyclic peptide libraries.' Chem & Biol. 8:801-815, 2001.*
Shoenfeld et al., "Efficacy of IVIG affinity-purified anti-double-stranded DNA anti-idiotypic antibodies in the treatment of an experimental murine model of systemic lupus erythematosus", International Immunology, 14(11 ): 1303-1311 (2002).
Evans, M. J., et al. Detection and Purification of Antiidiotypic Antibody Against Anti-DNA in Intravenous Immune Globulin. J. Clip. Immunol. (1991) 11:291-5.
Williams Jr., R, et al. Expression of F4, 8.12, 31, and 1616 Anti-DNA Idiotype-Related Antigens on Cationic Human IgG Myeloma Proteins. Clin. Immunol. and Immunopathology (1994) 73(2):215-223.

(Continued)

*Primary Examiner* — Nora Rooney
(74) *Attorney, Agent, or Firm* — Browdy and Neimark, PLLC

(57) ABSTRACT

Specific peptides have been discovered that mimic an idiotype of an autoantibody. Such peptides may be formed into polymers. The peptides may be used in pharmaceutical compositions for the treatment of an autoimmune disease together with a pharmaceutically acceptable excipient.

3 Claims, 2 Drawing Sheets

(56) References Cited

OTHER PUBLICATIONS

Waisman, A., et al. Modulation of murine systemic lupus erythematosus with peptides based on complementary determining regions of a pathogenic anti-DNA monoclonal antibody. Proc. Natl. Acad. Sci. USA—Immunology 94:4620-4625. (1997).

Minenkova, O., et al. Adam-HCV, a new-concept diagnostic assay for antibodies to hepatitis C virus in serum. Eur. J. Biochem. 268:4758-4768 (2001).

Sun, Y. Peptide mimicking antigenic and immunogenic epitome of double-stranded DNA in systemic lupus erythematosus. Intl. Immunol. 13(2):223-232 (2001).

Zhang, W. et al. Isolation of Human Anti-idiotypes Broadly Cross Reactive with Anti-dsDNA Antibodies.

Hoffman et al., "IVIG-bound IgG and IgM cloned by phage display from a healthy individual reveal the same restricted germ-line gene origin as in autoimmune thrombocytopenia" Clin. Exp. Immunol 121, 1:37-46 (2000).

"Epitope cloning of anti-idiotype antibodies using phage displayed antibodies" Fab library, Record of the Annual Meeting of the Japanese Society for Immunology, 28:46 (1998).

Jendreyko et al. "Genetic origin of IgG antibodies cloned by phage display and anti-idiotypic panning from three patients with autoimmune thrombocytopenia" Eur. J. Immunol, vol. 28, 12:4236-4247 (1998).

Wu et al., "Humanization of a Murine Monoclonal Antibody by Simultaneous Optimization of Framework and CDR Residues" J. Mol. Bioi. 294:151-62 (1999).

Masaki et ai.,"Epitope cloning of anti-idiotype antibodies using phage displayed antibodies" Fab library, Record of the Annual Meeting of the Japanese Society for Immunology, 28:46 (1998) (with English Translation).

Hermanson et al. "Immobilized Affinity Ligand Techniques" Academic Press Inc., San Diego, California, pp. 210-211 and pp. 313-314 (1992).

Experimental Medicine, Biomanual up series, Experimental method for molecular interaction of protein, Jul. 25. 1996, pp. 157-165 (with English Translation) Song et al. 'Autoantibodies in rheumatoid arthritis: rheumatoid factors and anticitrullinated protein antibodies.' QJM 103:139-146, 2010.

Mimouni et al. "Efficacy of intravenous immunoglobulin (IVI G) affinity-purified anti-desmoglein anti-idiotypic antibodies in the treatment of an experimental model of pemphigus vulgaris" Clin Exp Immunol 162:543-549 (2010).

Blanket al. "The efficacy of specific IVIG anti-idiotypic antibodies in antiphospholipids syndrome (APS): Trophoblast invasiveness and APS animal model" International Immunology 19:857-65 (2007).

Fuchs et al. "The Disease-Specific Arm of the Therapeutic Effect of Intravenous Immunoglobulin in Autoimmune Diseases: Experimental Autoimmune Myasthenia Gravis as a Model" IMAJ 10:58-60 (2008).

Silvestris et al., "Intravenous immune globulin therapy of lupus nephritis: use of pathogenic anti-DNA-reactive IgG," Clin Exp Immunol, 10 4(Suppl. 1) :91-97 (1996).

De Souza et al., "Anti-platelet autoantibodies from ITP patients recognize an epitope in GPIIb/IIIa deduced by complimentary hydropathy," Immunology 75:17-22 (1992).

Arepally and Ortel, "Heparin-induced thrombocytopenia," Annu. Rev. Med. 61:77-90 (2010).

Gniadecki, "Desmoglein autoimmunity and the pathogenesis of pemphigus," Autoimmunity 39:541-547 (2006).

Khosla et al., "Anti CCP antibodies in rheumatoid arthritis," J Indian Rheumatol Assoc 12:143-146 (2004).

Kalluri, "Good pasture syndrome" Kidney International, 55:1120-1122 (1999).

Table of Contents of a book entitled "Autoantibodies, Second Edition," edited by Shoenfeld et al., Elsevier, BV., Amsterdam, Netherlands, 2007.

Bradford. M. "A rapid and sensitive method for the quantitation of microgram quantities of protein utilizing the principle of protein-dye binding" Anal. Biochem 72:248-254 (1976).

Dietrich. G., et al Modulation of Autoimmunity by Intraveneous Immune Globulin through Interaction with the Function of the Immune/Idiotypic Network Clinical Immunology and Immunopathology 62(1): S73-S81 (1992).

Evans, M, et al In Vitro Modulation of Anti-DNA Secreting Peripheral Blood Mononuclear Cells of Lupus Patients by Anti-Idiotypic Antibody of Pooled Human Intravenous Immune Globulin Lupus 2(6):371-375 (1993).

Kent, S., High Yield Chemical Synthesis of Biologically Active Peptides on an Automated Peptide Synthesizer of Novel Design (Aimqvist & Wiksell, Stockholm) 185-188 (1984).

Maier, C.C. et al "Identification of Interactive Determinants on Idiotypic-Anti-idiotypic Antibodies through Comparison of their Hydrophatic Profiles" lmmunomethods 5:107-113 (1994).

Rossi, F. et al "Anti-Idiotypes against Autoantibodies in Normal Immunoglobulins: Evidence for Network Regulation of Human Autoimmune Responses" Immunological Reviews 110:135-149 (1989).

Schnolzer, M. et al "In situ neutralization in Bee-chemistry solid phase peptide synthesis" International Journal of Peptide and Protein Research (1992) 40(3-4):180-193 (1992).

Shoenfeld, Y. et al "Idiotypic Cross-Reactions of Monoclonal Human Lupus Autoantibodies" J. Exp. Med. 158(3): 99. 718-30.

Silvestris, F., et al 'Pathogenic anti-DNA idiotype-reactive IgG in intravenous immunoglobulin preparations' Clin Exp Immunol 97:19-25 (1994).

International Search Report re: PCT/IL03/00424 dated Nov. 13, 2003 Cwirla et al. 'Peptides on phage: A vast library of peptides for identifying ligands.' PNAS. 87:6378-6382, 1990.

Giebel et al. 'Screening of cyclic peptide phage libraries identifies ligands that bind streptavidin with high affinities.' Biochem. 34(47):15430-15435, 1995.

Wofsy et al. 'The Use of Affinity Chromatography for the Specific Purification of Antibodies and Antigens.' J. Immunol. 103(2):380-383 (1969).

Matsuoka, K., Protein-Protein Interactions Phage Display Screening, Experimental Medicine, Biomanual Up Series, Experimental Method for Molecular Interaction of Protein, pp. 35-39 (1996).

Nelson et al., Lehinger Principles of Biochemistry, Worth Publishers New York New York, p. 129 (2000).

Ph. D. Phage Display Peptide Library Kits, 4 pages (2004).

International Preliminary Examination Report re PCT/IL03/00424 dated Aug. 10, 2004.

Ph. D. Phage Display Peptide Library Kits, New England BioLabs, Inc., Technical Bulletin #E8100, E8110, E8120, pp. 1-8 (2004).

* cited by examiner

MOLECULES MIMICKING AN AUTOANTIBODY IDIOTYPE AND COMPOSITIONS CONTAINING SAME

FIELD OF THE INVENTION

This invention relates to the use of immunoglobulins purified from pooled plasma as a tool for the selection of synthetic molecules which mimic autoimmune self-antibodies and as a source for the isolation of specific antibodies for therapeutic use in autoimmune diseases.

BACKGROUND OF THE INVENTION

Autoimmune diseases such as systemic lupus erythematosus (SLE), myasthenia gravis (MG) and idiopathic thrombocytopenic purpura (ITP) occur when the immune system of an individual is triggered to recognize and attack self components. For example, SLE is a multisystemic autoimmune disease with a great diversity of clinical manifestations, ranging from mild clinical findings with typical abnormal laboratory tests, to a life-threatening condition. Laboratory abnormalities include high titers of autoantibodies to a vast array of tissue antigens. The most characteristic are those directed against components of the cell nucleus such as DNA, RNA, histones, nuclear proteins and protein-nucleic complexes. The clinical course of SLE is highly variable and unpredictable, frequently involving periods of remissions and relapses.

The survival of patients with SLE has improved remarkably over the past decades, mainly due to the use of corticosteroids and cytotoxic drugs. While such medications have powerful anti-inflammatory and immunomodulatory effects, their use is severely limited by immunosuppression, myelosuppression and/or numerous other frequent side effects. A safe and efficient mode of immunomodulatory therapy for this disorder is still lacking.

Intravenous immunoglobulin (IVIG) is a highly purified IgG preparation produced from pooled human plasma collected from thousands of healthy blood donors. It is known that IVIG can cause clinical improvement of patients suffering from autoimmune diseases. Administration of high dose intravenous immunoglobulin (IVIG) is immunoregulatory but not immunosuppressive or myelotoxic. IVIG is capable not only of modulating SLE in animal models and in humans but it also may provide a defense against infection rather than encouraging it. However, using IVIG in the treatment of SLE is at present limited by cost, a poor understanding of the mechanism of action and anecdotal reports presented in the literature regarding clinical efficacy.

Antibodies are classified into different classes based on the structure of their heavy chains. These include IgG, IgM, IgA and IgE. Antibodies having the same constant structure are considered as being of the same isotype. Antibodies of the same isotype having different antigenic determinants as a result of the inheritance of different alleles are called allotypes. Antigenic determinants in the variable regions of L and/or H chains that are associated with the antigen-binding site of an antibody are called idiotypes. Antibodies raised or which react against an idiotype are called anti-Idiotypic antibodies (anti-Id).

U.S. Pat. No. 4,690,905 (Diamond) discloses the preparation of monoclonal (mAB) anti-Id antibodies to human anti-DNA antibodies. The mABs bind a determinant present on anti-DNA antibodies of a plurality of SLE patients. The determinant is preferably outside the DNA binding site of the antibodies. Also disclosed are diagnostic reagents for the determination in serum of anti-native DNA antibodies, and therapeutic reagents which may be used in a method to remove anti-native DNA antibodies from the serum of patients suffering from SLE.

Shoenfeld Y, et al., (1983) J. Exp Med. 158(3):718-30 describes the evaluation of idiotypic cross-reactions in 60 polynucleotide-binding monoclonal lupus auto-antibodies produced by human-human hybridomas that were derived from seven unrelated patients with SLE. Three anti-idiotype reagents were prepared by immunization of rabbits or a mouse with monoclonal auto-antibodies from two patients. Binding of the three reagents to their corresponding idiotypes was inhibited by one or more polynucleotides, an indication that the anti-idiotypes reacted with the variable regions of the auto-antibodies. A monoclonal anti-idiotype reagent cross-reacted with autoantibodies from six of the seven patients, and was named 16/6. The idiotypic cross-reactions of immunoglobulins from unrelated patients suggest that the autoantibodies are derived from related families of germ line genes that are expressed by patients with SLE.

Evans, M. J. et al (1991) J. Clin. Immunol. 11:291-5 describes the preparation of anti-Id antibodies from pooled normal human IgG which bind to anti-DNA antibodies derived from sera of SLE patients. It is postulated that the therapeutic effect of IVIG on SLE patients may be due in part to the presence in IVIG of anti-Idiotype antibodies.

This hypothesis was further supported in a subsequent article by the same authors (Evans, M. and Abdou, N. I. (1993) Lupus 2:371-375) which describes the in vitro modulation of anti-DNA secreting peripheral blood mononuclear cells derived from lupus patients by anti-Id antibodies purified from IVIG.

Williams Jr., R. C., et al (1994) Clin. Immunol. Immunopath. 73:215-223 describes a number of idiotypic (Id) markers related to anti-DNA antibodies associated with SLE. These markers include 16/6, F4, 3I and 8.12. 43% of 100 cationic human IgG myeloma proteins isolated from patients with multiple myeloma were found to show the presence of at least one of the Id markers. It is stated that several of the anti-DNA Ids appear to be associated, but that the exact structural basis requires further study.

WO 96/30057 (Mazes) discloses synthetic peptides duplicating portions of the complementarity-determining region (CDR) of the heavy or light chains of a pathogenic anti-DNA Mab that induce SLE-like disease in mice (experimental SLE). Specifically, the sequences of 5 peptides of 12-30 amino acids are disclosed. Also disclosed is the use of such peptides for inhibiting the proliferative response of T-lymphocytes isolated from a SLE patient.

Waisman, A. et al (1997) Proc. Natl. Acad. Sci. 94:4620-4625 describes the synthesis and characterization of two peptides based on sequences of CDR1 and CDR3 of a pathogenic anti-DNA Mab that bears the 16/6 Id. The peptides were found to modulate experimental SLE in mice.

U.S. Pat. No. 6,231,856 (Williams) discloses a method for treating SLE by administrating an antibody composition comprising purified anti-Id antibodies that have specificity for idiotypic determinants located on anti-DNA antibodies (anti-DNA anti-Id). Also disclosed is a method for purifying anti-DNA anti-Id from IVIG In the method, anti-DNA myeloma antibodies from a patient with gamaglubonemia that express idiotypic determinants are bound to a solid phase. IVIG is passed through the solid phase, and the bound fraction is eluted, the bound fraction containing the anti-DNA anti-Id.

The Williams patent also discloses the possibility of preparing synthetic peptides capable of duplicating idiotypic determinants of self-reactive autoantibodies. Such determinants may be identified through a comparison of hydropathic profiles of idiotypic-anti-Idiotypic interaction based on a computer program, as is described in Maier, C. C. et al (1994) Immunomethods 5:107-113. These synthetic peptides maybe bound to a solid phase and used to purify anti-DNA anti-Id from IVIG, as described above.

Zhang, W. et al (2001) Scand. J. Immunol. 53:192-197 describes the isolation of human anti-Idiotypes from four SLE sera which were found to demonstrate broad cross reactivity to both polyclonal and monoclonal anti-DNA antibodies isolated from SLE patients. The anti-Idiotypes were isolated on a purified IgG anti-dsDNA F(ab')2 affinity column prepared from a single lupus patient.

Monaci, P. et al (2001) Europ. J. of Biochem. 268:4758-4768 describes the screening and identification of ligands using five random peptide phage display libraries and serum antibodies from noninfected individuals and patients infected by hepatitis C virus (HCV). Multimeric synthetic peptides that mimic several immunodominant epitopes of the virus were used to develop a diagnostic assay which detects antibodies to HCV in serum.

Sun, Y. et al (2001) Int. Immunol. 13:223-232 describes the use of anti-dsDNA antibodies isolated from the sera of SLE patients to screen a phage peptide library for peptides which mimic antigenic and immunogenic epitopes on dsDNA as mimotopes. The synthetic peptide mimotope had the sequence RLTSSLRYNP (SEQ ID NO:1), and was recognized by 88% of anti-dsDNA antibody-positive SLE sera which cross react with ssDNA.

SUMMARY OF THE INVENTION

It is an object of the present invention to provide molecules which mimic antigenic determinants present in antibodies associated with autoimmune disease.

It is a further object of the invention to provide a method for preparing such molecules.

It is a still further object of the invention to provide a method for preparing anti-Idiotypic antibodies which may be used to treat autoimmune disease.

In a first aspect of the invention, there is provided a method for identifying molecules which mimic an idiotype of an autoimmune disease-associated auto-antibody (autoantibodies), comprising:
(a) purifying autoantibodies from sera of one or more patients afflicted with the autoimmune disease;
(b) binding the autoantibodies to a solid phase to form an affinity matrix;
(c) contacting pooled plasma or B cells comprising immunoglobulins with the affinity matrix followed by removal of unbound plasma components;
(d) eluting bound immunoglobulins, being anti-Idiotypic antibodies (anti-Id) to autoantibodies, from the matrix;
(e) providing a molecular library comprising a plurality of molecule members; and
(f) contacting the anti-Id with the molecular library and isolating those bound molecules which are bound by the anti-Id, the bound molecules being molecules which mimic an idiotype of autoantibodies.

The present invention is based on the isolation of molecules which mimic antigenic determinants present in antibodies associated with autoimmune disease, unlike previously-described methods which isolate molecules which mimic antigenic determinants present in a disease-associated antigen rather than in the antibody which binds the antigen.

The method of the present invention differs from previously-known methods in that the molecules and antibodies of the invention are prepared without coming into contact with sera taken from diseased individuals, so that the products are safe for administration to patients.

In the context of this specification, the following terms shall have the meaning following them unless otherwise indicated:

Autoimmune disease is a consequence of a cellular and a humoral response to self-antigens. A humoral dominant autoimmune condition includes a disease, illness, disorder or syndrome, in the course of which the patient produces antibodies that bind one or more of the patient's own epitopes, whether it is known today to be so or that may be diagnosed as such in the future.

The autoimmune diseases known to date include any disease mentioned in the background of the invention and any of the following: Myasthenia Gravis (MG), Congenital myasthenia gravis, Multiple sclerosis (MS), Stiff-man syndrome, Tropical spastic paraparesis, Rasmussen's encephalitis, Acute motor axonal neuropathy, Acute sensory-motor axonal neuropathy, Dorsal root ganglion neuritis, Acute pan-autonomic neuropathy, Brachial neuritis, Acute necrotizing hemorrhagic lekoencephalitis, Sporadic necrotizing myelopathy, Paraneoplastic cerebellar degeneration, Guillain-Barre syndrome, Limbic encephalitis, Opsoclonus-myoclonus ataxia, Sensory neuronitis, Autonomic neuropathy, Demyelinating neuropathy, AIDS-dementia complex, Tourette's syndrome, Miller-Fisher syndrome, Alzheimer's disease, Graves' Disease, Hashimoto's thyroiditis, Postpartum thyroiditis, Focal thyroiditis, Juvenile thyroiditis, Idiopathic hypothyroidism, Type I (insulin dependent) diabetes mellitus, Addison's disease, Hypophysitis, Autoimmune diabetes insipidus, Hypoparathyroidism, Pemphigus Vulgaris, Pemphigus Foliaceus, Bullous phemphigoid/Pemphigoid gestationis, Cicatrical pemphigoid, Dermatitis herpetiformis, Epidermal bullosa acquisita, Erythema multiforme, Herpes gestatonis, Vitiligo, Chronic urticaria, Discoid lupus, Alopecia universalis/Areata, Psoriasis, Autoimmune hepatitis, Primary biliary cirrhosis, Chronic active hepatitis, Chronic active hepatitits/Primary biliary cirrhosis overlap syndrome, Primary sclerosing cholangitis, Autoimmune hemolytic anemia, Idiopathic thrombocytopenic purpura, Evans syndrome, Heparin-induced thrombocytopenia, Primary autoimmune neutropenia, Autoimmune (primary) neutropenia of infancy, Autoimmune neutropenia following bone marrow transplant, Acquired autoimmune hemophilia, Autoimmune gastritis and pernicious anemia, Coeliac disease, Crohn's disease, Ulcerative colitis, Sialadenitis, Autoimmune premature ovarian failure, Azoospermia, Hypogonadism, Male infertility associated with sperm autoantibodies, Autoimmune orchitis, Premature ovarian failure, Autoimmune oophoritis, Uveitis, Retinitis, Sympathetic ophthalmia, Birdshot retinochoroidopathy, Vogt-Koyanagi-Harada granulomatous uveitis, Retinal degeneration, Lens-induced uveitis, Optic neuritis, Autoimmune sensorineural hearing loss, Meniere's disease, Autoimmune myocarditis, Congenital heart block (neonatal lupus), Chagas' disease, Adriamycin cardiotoxicity, Dressler's myocarditis syndrome, Bronchial asthma, Interstitial fibrosing lung disease, Rapidly progressive glomerulonephritis, Autoimmune tubulointerstitial nephritis, Systemic lupus erythematosus (SLE), Antiphospholipid syndrome, Rheumatoid arthritis, Juvenile Rheumatoid arthritis, Felty's syndrome, Large granular lymphocytosis (LGL), Sjogren's syndrome, Systemic sclerosis (scleroderma), Crest syndrome, Mixed connective tissue disease, Polymyositis/dermatomyositis, Goodpasture's Disease, Wegener's granulomatosis, Churg-Strauss syndrome, Henoch-Schonlein purpura, Microscopic polyangiatis, Periarteritis nodosa, Bechet's syndrome, Atherosclerosis, Temporal (giant) cell arteritis, Takayasu arteritis, Kawasaki disease, Ankylosing spondilitis, Reiter's disease, Sneddons disease, Autoimmune polyendocrinopathy, candidiasis-ectodermal dystropy, Essential cryoglobulinemic vasculitis, Cutaneous leukocytoclastic angiitis, Lyme disease, Rheumatic fever and heart disease, Eosinophilic fasciitis, Paroxysmal cold hemoglobinuria, Polymyalgia rheumatica, Fibromyalgia, POEMS syndrome (polyneuropathy, organomegaly, endocrinopathy, M-spot and skin changes), Relapsing polychondritis, Autoimmune lymphoproliferative syndrome, TINU syndrome (acute tubulointerstitial nephritis and uveitis), Common variable immunodeficiency, TAP (transporter associated with antigen presentation) deficiency, Omenn syndrome, HyperIgM syndrome, BTK agammaglobulinemia, Human immunodeficiency virus and Post bone-marrow-transplant.

An autoimmune-disease associated auto-antibody (autoantibody) is any antibody produced by the body against self-antigens and implicated in or associated with the etiology or symptoms of an autoimmune disease.

Molecules are any molecule, organic or inorganic, synthetic or natural, including, by way of example, peptides, proteins and combinatorial chemicals, as well as dimers, oligomers or polymers (n=2 or more) of each of the above, e.g. based on a poly lysine backbone or other chemical platform, whether alone or in conjunction with other molecules. In the case of peptides and proteins, the term molecules also includes derivatives of the peptides and proteins in which one or more amino acids have been added, deleted or replaced without substantially affecting the mimic function of the molecule.

Mimic in the context of this invention means having the capability of reproducing the three-dimensional (3D) conformation of an epitope without necessarily duplicating its structure. This mimicry need not be a complete duplication, and may be also an approximation thereof which is sufficiently similar to that of the original idiotype so that the mimicking molecule would be bound by the same anti-Id antibody as the original idiotype.

Pooled plasma means plasma containing immunoglobulins pooled from a plurality of healthy subjects, and fractions thereof. One skilled in the art of the invention will appreciate that such pooled plasma may include without limitation any immunoglobulin-containing fraction of the pooled plasma. Any partially purified or purified fraction of the pooled plasma may be used according to the invention. In a preferred embodiment, the pooled plasma is IVIG or any derivative thereof. Also contemplated within the scope of the invention are pooled, stimulated B-cells and pooled organs that are rich in immunoglobulins such as breast (colostrum), kidneys, lung or brain.

Molecular library in the context of this invention means any library that provides a collection of molecules from which one may select one or more molecules which mimic the idiotype of choice according to the invention. Many such libraries are readily available, including for example, peptide phage display libraries, combinatorial chemical libraries, single chain antibody libraries, ribosomal libraries, etc.

A patient means any person afflicted with an autoimmune disease, regardless of the phase or progress of the disease in the person, and regardless of whether or not the person is being treated for the disease or any of its symptoms. Thus, a patient may be suffering either from an active phase of the disease (i.e. when the symptoms of the disease are manifested) or in remission (i.e. when the person appears to be healthy).

It will be appreciated that the autoantibodies may be collected from a single patient or from a specific sub-group of patients. This will enable, according to the invention, the identification of mimicking molecules that correspond with the specific sub-class of the autoimmune disease from which the donors suffer. Alternatively, collection of autoantibodies from an unclassified plurality of patients may allow the identification of mimic molecules that correspond to a plurality of different classes of the same autoimmune disease, characterized for example by different prognoses.

The solid phase used to form the affinity matrix according to the invention, may be any appropriate solid phase known in the art such as epoxy or formil groups, in any appropriate form such as a column, magnetic beads or filters. The solid phase will generally be activated so as to enable the autoantibodies to bind thereto. Examples of activation include, but are not limited to, CNBr-activation and periodate-oxidation.

According to one preferred embodiment of the invention, the autoimmune disease is SLE. It is established that, at least in some autoimmune diseases, the patients providing the autoantibodies may be afflicted with either an active phase of the autoimmune disease or may be in remission. Accordingly, the amounts and types of autoantibodies obtained may differ, providing different sets of mimicking molecules.

According to a preferred embodiment of the invention, the molecular library is a peptide phage display library. Such phage display library may display, for example, peptides comprising three or more amino acids, or, for example, cyclic peptides. Use of such a library would provide peptides that mimic idiotypes of autoantibodies, and the sequence (whether amino acid or nucleic acid) of such peptides can be easily obtained from the same library according to known methods. In other embodiments, the molecular library may be a combinatorial chemical library or a single chain antibody library.

A person skilled in the art will further appreciate that the pooled plasma may be brought into contact with a series of affinity matrices, each affinity matrix having bound thereto autoantibodies from a different autoimmune disease, or from different manifestations of one autoimmune disease. Thus, from the one sample of pooled plasma one may identify different mimicking molecules without need to collect pooled plasma again for each autoimmune disease. This would allow for more efficient and economic use of the pooled plasma.

According to a second aspect of the invention, there is provided a molecule which mimics an idiotype of an autoantibody, the molecule excluding the following peptides:

```
                                        (SEQ ID NO: 2)
(a) VAYISRGGVSTYYSDTVKGRFTRQKYNKRA (SEQ ID NO: 3)
(b) TEKLRLRYFDYYG (SEQ ID NO: 4)
(c) LVKPGGSLKLSCAASGFT (SEQ ID NO: 5)
(d) RLEWVATISGDGGSYT (SEQ ID NO: 6)
(e) KGRFTISRDNAKNTLYL
```

-continued (f) MNWVKQSHGKSL (SEQ ID NO: 7)

(g) FYNQKFKGKATL (SEQ ID NO: 8)

(h) SEDSALYYCARD (SEQ ID NO: 9)

(i) YYYGAGSYYKRGYFD (SEQ ID NO: 10)

(j) TGYYMQWVKQSPEKSLEWIG (SEQ ID NO: 11)

(k) YYCARFLWEPYAMDYWGQGS (SEQ ID NO: 12)

(l) EINPSTGGTTYNQKFKAKAT (SEQ ID NO: 13)

(m) GYNMNWVKQSHGKSLEWIG (SEQ ID NO: 14)

(n) YYCARSGRYGNYWGQTL (SEQ ID NO: 15)

A person skilled in the art of the invention would appreciate that the above mentioned molecules may be prepared by steps a-f of the method described above for identifying molecules which mimic idiotypes of an autoantibody.

By one example of the invention, 33 such peptides were prepared and were discovered to have the following sequences:

(a) KHETTET (SEQ ID NO: 16)

(b) PPNHSHL (SEQ ID NO: 17)

(c) AGLKNSQ (SEQ ID NO: 18)

(d) ASTIRAG (SEQ ID NO: 19)

(e) PLSSSLP (SEQ ID NO: 20)

(f) FLTLTEL (SEQ ID NO: 21)

(g) VRVLLRS (SEQ ID NO: 22)

(h) SQLGMVS (SEQ ID NO: 23)

(i) SEHTTVH (SEQ ID NO: 24)

(j) TQPPELP (SEQ ID NO: 25)

(k) LSQPERW (SEQ ID NO: 26)

(l) PPPDLHA (SEQ ID NO: 27)

(m) EESSYLV (SEQ ID NO: 28)

(n) SNEQMLY (SEQ ID NO: 29)

(o) SASFTMI (SEQ ID NO: 30)

(p) GTTQWVL (SEQ ID NO: 31)

(q) HSLTQPA (SEQ ID NO: 32)

(r) QLALHST (SEQ ID NO: 33)

(s) YGTPSSE (SEQ ID NO: 34)

(t) KMHSVGS (SEQ ID NO: 35)

(u) SLQRHPW (SEQ ID NO: 36)

(v) FEVASLP (SEQ ID NO: 37)

(w) GDSLRST (SEQ ID NO: 38)

(x) NSRDSSE (SEQ ID NO: 39)

(y) PLPDWRV (SEQ ID NO: 40)

(z) VGALPLE (SEQ ID NO: 41)

(aa) TQEPSPL (SEQ ID NO: 42)

(bb) DWLYSRS (SEQ ID NO: 43)

(cc) LRVSTTE (SEQ ID NO: 44)

(dd) PPQKHLL (SEQ ID NO: 45)

(ee) EMTATVS (SEQ ID NO: 46)

(ff) VRLEGLP (SEQ ID NO: 47)

(gg) KYKRKYP (SEQ ID NO: 48)

Such a molecule may also be in the form of a polymer.

According to a third aspect, the invention provides a method for treating a patient afflicted with an autoimmune disease comprising administering to the patient an effective amount of a molecule according to the invention.

According to a still further aspect of the invention, there is provided a pharmaceutical composition for the treatment of an autoimmune disease comprising an effective amount of a molecule according to the invention together with a pharmaceutically acceptable excipient. Such excipients are well known to the skilled man of the art.

According to another aspect, the invention provides a method for screening chemical compounds for their potential use in treating an autoimmune disease comprising (a) providing a molecule which mimics an idiotype of an autoimmune disease, excluding the following peptides:

VAYISRGGVSTYYSDTVKGRFTRQKYNKRA (SEQ ID NO: 2)

TEKLRLRYFDYYG (SEQ ID NO: 3)

LVKPGGSLKLSCAASGFT (SEQ ID NO: 4)

RLEWVATISGDGGSYT (SEQ ID NO: 5)

KGRFTISRDNAKNTLYL (SEQ ID NO: 6)

MNWVKQSHGKSL (SEQ ID NO: 7)

FYNQKFKGKATL (SEQ ID NO: 8)

SEDSALYYCARD (SEQ ID NO: 9)

YYYGAGSYYKRGYFD (SEQ ID NO: 10)

TGYYMQWVKQSPEKSLEWIG (SEQ ID NO: 11)

YYCARFLWEPYAMDYWGQGS; (SEQ ID NO: 12)

(b) bringing the screened chemical compounds into contact with the molecule; and (c) identifying a compound which binds to the molecule, the binding compound having a potential use in treating an autoimmune disease.

It will be appreciated by one skilled in the art of the invention, that the binding of the molecule to the chemical compound may be achieved by many different methods as appropriate to the molecule and compound of choice, including, for example, variation of binding conditions (e.g., salt concentration, pH, etc.).

According to another aspect, the invention provides a method for the preparation of anti-Id to autoantibodies, wherein the anti-Id have not been brought into contact with proteins derived from sera of autoimmune disease patients, comprising the following steps:
(a) purifying autoantibodies from sera of one or more patients afflicted with the autoimmune disease;
(b) binding the autoantibodies to a solid phase to form an affinity matrix;
(c) contacting pooled plasma comprising immunoglobulins with the affinity matrix followed by removal of unbound plasma components;
(d) eluting bound immunoglobulins, being anti-Idiotype antibodies (anti-Id) to autoantibodies, from the matrix;
(e) providing a molecular library comprising a plurality of molecule members; and
(f) contacting the anti-Id with the molecular library and isolating those bound molecules which are bound by the anti-Id, the bound molecules being molecules which mimic idiotypes of autoantibodies;
(g) binding one or more of the bound molecules to a solid phase to form a second affinity matrix;
(h) contacting pooled plasma comprising immunoglobulins with the second affinity matrix followed by removal of unbound plasma components;
(i) eluting the bound immunoglobulins, being a second anti-Id to autoantibodies, from the second matrix, the second anti-Id not having been brought into contact with proteins derived from sera of autoimmune disease patients.

In a preferred embodiment, the pooled plasma is IVIG.

Unlike the first anti-Id of step (d), the second anti-Id have not come into contact with sera of plasma components of patients afflicted with an autoimmune disease. This renders the second anti-Id safer for administration than the first anti-Id, as the danger of contamination of the second anti-Id by plasma components of unhealthy individuals is removed.

It will be appreciated by a person skilled in the art of the invention that the second anti-Id could be useful in a method for treating a patient afflicted with an autoimmune disease. Such method comprises administering to the patient an effective amount of such anti-Id.

According to another aspect of the invention, there is provided a method for the preparation of anti-Id to autoantibodies comprising immunizing an animal with an effective amount of a molecule according to the invention.

According to a further aspect, the invention provides a method for identifying a specific idiotype of an autoantibody comprising the following steps:
(a) providing a series of anti-Id of known idiotypic specificity according to this invention;
(b) bringing the autoantibodies into contact with the series of anti-Id; and
(c) identifying an anti-Id which binds to the autoantibodies, the idiotype of the bound anti-Id being the idiotype of the autoantibodies.

This method can be useful in diagnosis of the specific autoantibodies in a patient, or a class of patients. A person skilled in the art of the invention would appreciate that such identification may be useful for characterization of different aspects of the disease, providing prognoses to different patients and ultimately in the treatment of the patients. Having identified the specific idiotype of an autoantibody in a patient may allow choosing a specific class of molecules or anti-Id according to this invention for treatment of the patient.

According to a still further aspect, the invention provides a method for manufacturing purified human anti-Id immunoglobulins comprising the following steps:
(a) immunizing a subject with a molecule according to the invention;
(b) collecting sera from the subject; and
(c) purifying human anti-Id immunoglobulins from the sera.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF AN EMBODIMENT

Example I

Figure 1:
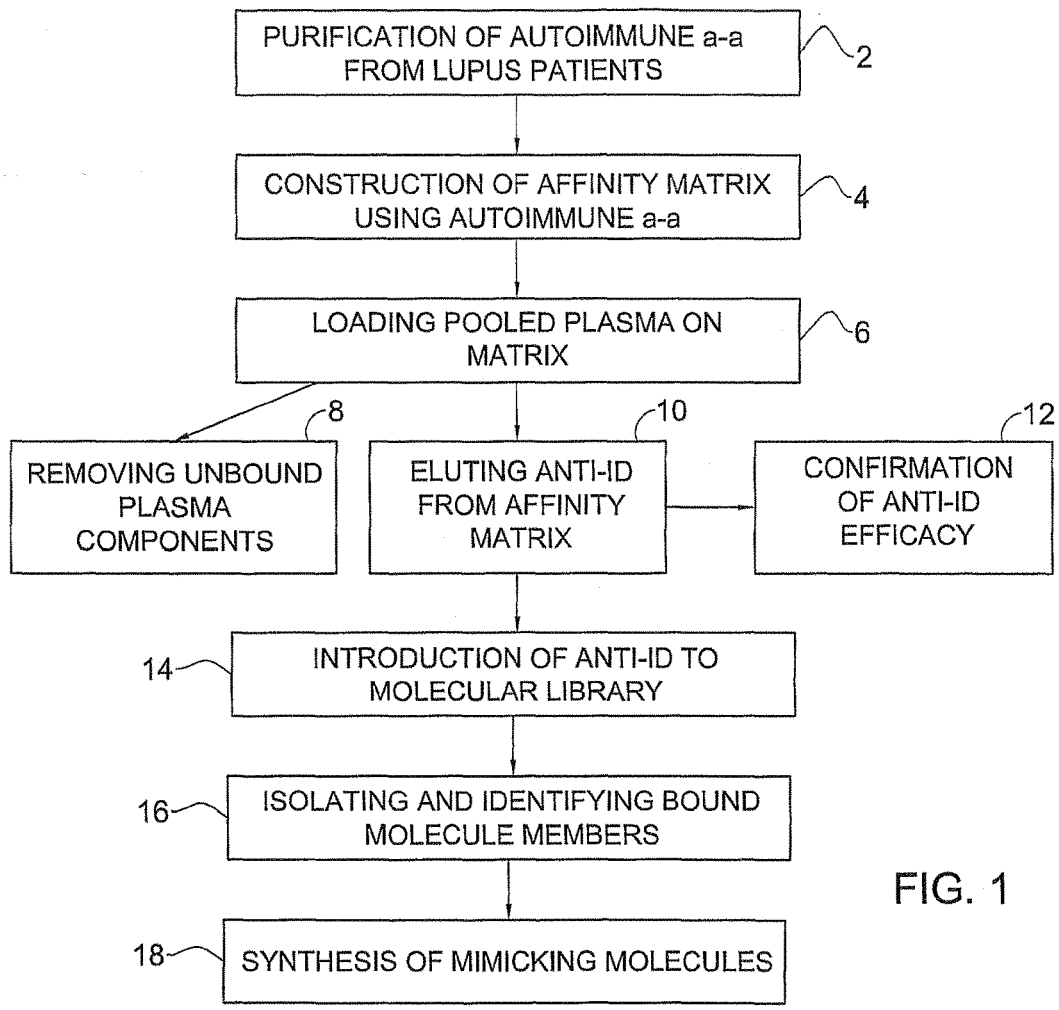
FIG. 1 is a flow chart showing one embodiment of a method according to the invention for identifying molecules which mimic idiotypes of an autoantibody.

One embodiment of a method for identifying molecules which mimic idiotypes of an autoimmune-a-a is illustrated in FIG. 1.

The first step of the method, indicated in FIG. 1 by reference numeral 2, involves purifying autoantibodies from sera of one or more patients afflicted with the autoimmune disease. For example, anti-double-stranded DNA (anti-ds-DNA) antibodies may be purified from several tens of patients suffering from SLE (lupus patients). In the next step 4, the autoantibodies are bound to a solid phase to form an affinity matrix. Following the above example, the anti-dsDNA antibodies are bound to a CNBr-activated Sepharose column.

The following step 6 comprises contacting pooled plasma comprising immunoglobulins with the affinity matrix followed by the step 8 of removal of unbound plasma components. In the example, IVIG is loaded on the affinity column which is subsequently washed to remove unbound immunoglobulins. Only the immunoglobulins which bind the anti-dsDNA antibodies remain bound to the column.

In the next step 10, the bound anti-Idiotype antibodies (=anti-Id) are eluted from the affinity matrix. In the example, these would be anti-anti-dsDNA anti-Idiotypes. The efficacy of the anti-Id may be confirmed 12, for example by in vitro tests and in vivo using a lupus experimental model.

In the following step 14, a molecular library is provided comprising a plurality of molecule members, and the eluted anti-Id is brought into contact with the molecular library. Those molecules which are bound by the anti-Id are isolated and identified 16. These molecules mimic an idiotype of the autoantibodies. In the above example, the anti-dsDNA antibodies are introduced to a C7C-peptide phage display library, and the peptides bound by the antibodies are isolated and identified. These peptides mimic idiotypes of the anti-dsDNA antibodies. Mimicking peptides may then be synthesized 18.

Example II

Figure 2:
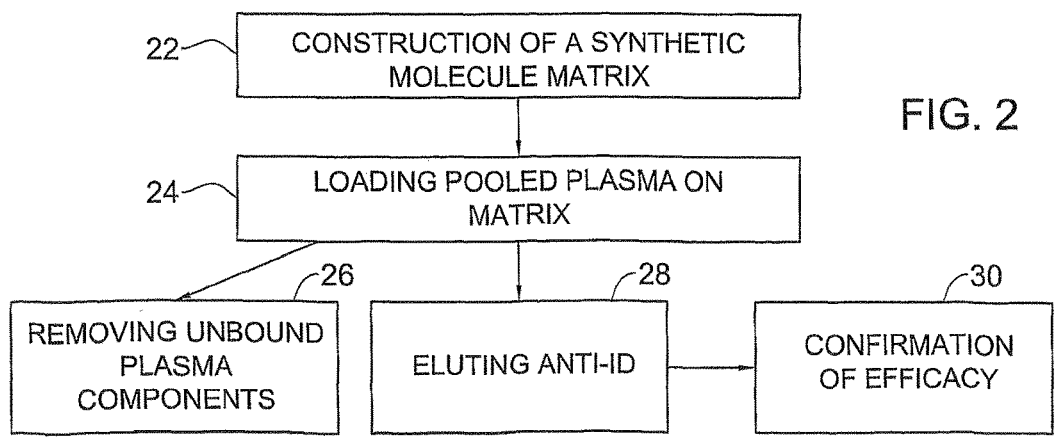
FIG. 2 is a flow chart showing one embodiment of a method according to the invention for preparation of anti-Id to autoantibodies.

One embodiment of a method for preparation of anti-Id to autoantibodies is illustrated in FIG. 2.

In the first step 22, an affinity matrix is prepared by binding the mimicking molecules obtained by the method illustrated in FIG. 1 to a solid phase to form a second affinity matrix. The mimicking molecules may be those isolated from the molecular library, or other molecules synthesized on the basis of the isolated molecules. Following the example given with respect to FIG. 1, these would be peptides which mimic idiotypes of the anti-dsDNA antibodies.

In the next step 24, pooled plasma comprising immunoglobulins is contacted with this second affinity matrix followed by removal 26 of unbound plasma components. In the example, IVIG is loaded on the column which is subsequently washed to remove unbound immunoglobulins. In the following step 28, the anti-Id is eluted from the affinity matrix. The efficacy of the anti-Id may be confirmed 30, for example by in vitro tests and in vivo using a lupus experimental model. These second anti-Id are safe for use in the treatment of patients, not having been brought into contact with proteins derived from sera of autoimmune disease patients. For example, they may be used to treat lupus patients.

Example III

Identification of Molecules, which Mimic Idiotypes of an Autoantibody

1. Materials and Methods

Anti-anti-dsDNA (anti-Id) isolated from IVIG as described above in Example I was employed to detect specific peptides presented by M13 phages. A commercial Ph.D.7™ phage display library (cat. number E8100S, New England Biolabs Inc) was used according to the manufacturer's procedure, slightly modified by the inventors, as follows:

Anti-Id in 50 mM NaHCO3 (Ph 8.5) was biotinylated by adding Sulfo-NHS-LC-Biotin (Pierce #21335), incubated 2 hrs on ice and dialyzed against 2% maltose. The efficacy of biotinylation was assayed by ELISA on neutravidine coated plates.

Biotinylated (1 µg) was introduced to the peptide phage display library (10 µg-2×1011 pfu) overnight at 4° C. The mixture was subjected to streptavidin coated petri-dish (3 cm, Nunc) blocked with 3% BSA. Following 20 minutes of incubation, the non-specific low affinity binding between streptavidin and the phages was prevented by adding biotin 0.1 mM for 5 min. Following extensive washings with TBS/Tween, the bound phages were eluted with Glycine-HCl 0.2M pH 2.3 and immediately neutralized with Tris pH 9.

The eluted phages were introduced to an ER2738 E. Coli host strain at a mid-log phase (OD600~0.5) and incubated at room temperature for 5 min to allow the phages to enter the bacteria; then incubated for 4.5 hrs for replication and the bacteria were sedimented by centrifugation. The phages were isolated from the supernatant by incubation with PEG-8000 1:5 at 4° C. The amplified phages were incubated again with the original biotinylated anti-Id for the second round. Finally, 5 rounds of amplification procedure was performed using the same procedure. Between each round, the phages again undergo panning on Fe coated plates to maximally delete the Fc binding phages.

The eluted phages from the last round, at 10-fold serial dilutions, were mixed with top-agarose and plated on LB/IPTG/XGAL plates. The blue plaques were collected, and each plaque was grown separately for 4.5 hrs in 10 ml LB for phage collection and centrifuged. The phages were isolated from the cultures by incubating the supernatant with PEG-8000 1:5.

The 847 colonies were screened for recognition by anti-Id by ELISA. Plates (96 wells) were coated with goat-anti-M13, blocked with 3% BSA and hemocyanin, and incubated with the phages. The binding was probed with biotinylated anti-Id or biotinylated individual IgG (from one person as negative control) followed by exposure to streptavidin-alkaline phosphatase and an appropriate substrate. Finally 33 clones were found to be significantly positive for anti dsDNA anti-Id and were not recognized by IgG affinity-purified from one healthy donor.

The positive clones were introduced to ER2738 E. Coli host strain for amplifying the phages 5.5 hrs for DNA preparation, using QIAprep M13 (QIAGENE cat. no 27704) according to the manufacturer's procedure. Briefly, the supernatant was separated into 1.4 ml for small DNA preps and the rest for introduction to ER2537(1:100 diluted bacteria ER2537 from the overnight culture) in LB. Precipitation solution was added into the 1.4 ml supernatant tubes, vortexed and left for 7 min at RT. The mix was loaded onto minicolumn/2 ml tubes, in 2 rounds of 700 ul/minicolumn. The tubes were centrifuged for 15 sec at 8,000 rpm at RT, after the first and second loading. Lysis buffer was added to the columns (700 ul/column), incubated 1 min at RT and centrifuged. Washing buffer was added 700 ul/column and the columns were centrifuged 15 see, 8,000 rpm at RT, the liquid was discharged and the columns were centrifuged again. The columns were attached to sterile tubes. Pre-warmed (50° C.) elution buffer was added onto the columns (50 ul/column). The columns were incubated 10 min at RT, and centrifuged 2 min at 14,000 rpm at RT.

The DNA preparations were sequenced by mbc Company, Nes-Ziona, Israel.

The peptides were synthesized as cyclic peptides at The Weizmann Institute, Rehovot, Israel. The peptide sequences are listed in Table 1:

TABLE 1

List of synthetic peptides synthesized:

(a) KHETTET (SEQ ID NO: 16)
(b) PPNHSHL (SEQ ID NO: 17)
(c) AGLKNQ (SEQ ID NO: 18)
(d) ASTIRAG (SEQ ID NO: 19)
(e) PLSSSLP (SEQ ID NO: 20)
(f) FLTLTEL (SEQ ID NO: 21)
(g) VRVLLRS (SEQ ID NO: 22)
(h) SQLGMS (SEQ ID NO: 23)
(i) SEHTTVH (SEQ ID NO: 24)
(j) TQPPELP (SEQ ID NO: 25)
(k) LSQPERW (SEQ ID NO: 26)
(l) PPPDLHA (SEQ ID NO: 27)
(m) EESSYLV (SEQ ID NO: 28)
(n) SNEQMY (SEQ ID NO: 29)
(o) SASFTMI (SEQ ID NO: 30)
(p) GTTQWL (SEQ ID NO: 31)
(q) HSLTQPA (SEQ ID NO: 32)
(r) QLALHST (SEQ ID NO: 33)

TABLE 1-continued

List of synthetic peptides synthesized:

(s) YGTPSSE (SEQ ID NO: 34)
(t) KMHSVS (SEQ ID NO: 35)
(u) SLQRHW (SEQ ID NO: 36)
(v) FEVASLP (SEQ ID NO: 37)
(w) GDSLRST (SEQ ID NO: 38)
(x) NSRDSSE (SEQ ID NO: 39)
(y) PLPDWV (SEQ ID NO: 40)
(z) VGALPLE (SEQ ID NO: 41)
(aa) TQEPSPL (SEQ ID NO: 42)
(bb) DWLYSRS (SEQ ID NO: 43)
(cc) LRVSTTE (SEQ ID NO: 44)
(dd) PPQKHLL (SEQ ID NO: 45)
(ee) EMTATVS (SEQ ID NO: 46)
(ff) VRLEGLP (SEQ ID NO: 47)
(gg) KYKRKP (SEQ ID NO: 48)

2. Direct Binding of Anti-Id to the Synthetic Peptides:

The binding of anti-Id to the peptides was tested by ELISA.

ELISA plates were coated by 1 Oug/ml of peptides in PBS overnight at 4° C. The plates were blocked with 3% BSA for 1 hr at 37° C. Anti-Id was added at different concentrations. IgG purified from one donor was used as negative control.

The binding of the immunoglobulin was probed with goat anti-human IgG conjugated to alkaline phosphatase and the appropriate substrate. Between each step, extensive washings were performed with 0.05% PBS-Tween.

The following peptides were used:

(1) KHETTET (SEQ ID NO: 16)
(2) PPNHSHL (SEQ ID NO: 17)
(3) AGLKNSQ (SEQ ID NO: 18)
(4) ASTIRAG (SEQ ID NO: 19)
(5) VRVLLRS (SEQ ID NO: 22)

-continued (6) TQPPELP (SEQ ID NO: 25)

(7) LSQPERW (SEQ ID NO: 26)

(8) PPPDLHA (SEQ ID NO: 27)

(9) GTTQWVL (SEQ ID NO: 31)

(10) YGTPSSE (SEQ ID NO: 34)

(11) SLQRHPW (SEQ ID NO: 36)

(12) PLPDWRV (SEQ ID NO: 40)

(13) DWLYSRS (SEQ ID NO: 43)

(14) PPQKHLL (SEQ ID NO: 45)

(15) KYKRKYP (SEQ ID NO: 48)

The binding results (OD at 405 nm) are presented in Table 2.

TABLE 2

| μg/ml | anti-Id | | | | control IgG | |
|---|---|---|---|---|---|---|
| | 10 | 5 | 2.5 | 1 | 5 | 1 |
| Pep 1 | 1.815 | 1.329 | 0.269 | 0.046 | 0.016 | 0.013 |
| Pep 2 | 2.063 | 1.296 | 0.256 | 0.041 | 0.009 | 0.009 |
| Pep 3 | 1.444 | 0.804 | 0.155 | 0.042 | 0.011 | 0.011 |
| Pep 4 | 1.648 | 0.926 | 0.184 | 0.041 | 0.011 | 0.013 |
| Pep 5 | 2.036 | 1.356 | 0.284 | 0.039 | 0.008 | 0.009 |
| Pep 6 | 2.051 | 1.182 | 0.228 | 0.049 | 0.009 | 0.007 |
| Pep 7 | 1.457 | 0.316 | 0.093 | 0.045 | 0.048 | 0.045 |
| Pep 8 | 1.319 | 0.258 | 0.074 | 0.05 | 0.046 | 0.043 |
| Pep 9 | 1.125 | 0.235 | 0.067 | 0.043 | 0.044 | 0.045 |
| Pep 10 | 2.539 | 0.695 | 0.14 | 0.048 | 0.048 | 0.06 |
| Pep 11 | 1.798 | 0.487 | 0.148 | 0.066 | 0.068 | 0.068 |
| Pep 12 | 1.356 | 0.273 | 0.072 | 0.042 | 0.045 | 0.043 |
| Pep 13 | 0.748 | 0.387 | 0.099 | 0.112 | 0.078 | 0.069 |
| Pep 14 | 0.987 | 0.611 | 0.234 | 0.113 | 0.083 | 0.079 |
| Pep 15 | 0.287 | 0.117 | 0.067 | 0.049 | 0.068 | 0.037 |

3. Direct Binding Synthetic Peptides:

The same protocol was used as above, but the peptides used in this study were taken from the literature except for peptide number 1 which is the first peptide in the previous experiment.

The peptides used were:
(1) KHETTET (SEQ ID NO:16)
(2) TGYYMQWVKQSPEKSLEWIG (SEQ ID NO:11)
(3) YYCARFLWEPYAMDYWGQGS (SEQ ID NO:12)
(4) VAYISRGGVSTYYSDTVKGRFTRQKYNKRA (SEQ ID NO:2)
(5) TGYYMQWVKQSPEKSLEWIG (SEQ ID NO:11)
(6) YYCARFLWEPYAMDYWGQGS (SEQ ID NO:12)
(7) TEKLRLRYFDYYG (SEQ ID NO:3)
(8) LVKPGGSLKLSCAASGFT (SEQ ID NO:4)
(9) MNWVKQSHGKSL (SEQ ID NO:7)
(10) FYNQKFKGKATL (SEQ ID NO:8)
(11) YYYGAGSYYKRGYFD (SEQ ID NO:10)

TABLE 3

| μg/ml | anti-Id | | | | Control IgG | |
|---|---|---|---|---|---|---|
| | 10 | 5 | 2.5 | 1 | 5 | 1 |
| Pep 1 | 1.21 | 0.216 | 0.074 | 0.041 | 0.043 | 0.044 |
| Pep 2 | 1.701 | 0.357 | 0.105 | 0.047 | 0.041 | 0.04 |
| Pep 3 | 0.965 | 0.164 | 0.065 | 0.041 | 0.043 | 0.043 |
| Pep 4 | 0.518 | 0.092 | 0.0475 | 0.044 | 0.039 | 0.04 |
| Pep 5 | 0.732 | 0.128 | 0.054 | 0.046 | 0.048 | 0.043 |
| Pep 6 | 1.634 | 0.342 | 0.082 | 0.044 | 0.043 | 0.046 |
| Pep 7 | 0.38 | 0.105 | 0.055 | 0.056 | 0.052 | 0.043 |
| Pep 8 | 1.413 | 0.211 | 0.088 | 0.041 | 0.041 | 0.044 |
| Pep 9 | 0.037 | 0.095 | 0.045 | 0.041 | 0.045 | 0.044 |
| Pep 10 | 0.231 | 0.059 | 0.041 | 0.036 | 0.041 | 0.042 |
| Pep 11 | 0.547 | 0.098 | 0.047 | 0.043 | 0.041 | 0.043 |

4. Percent Inhibition with Mix Cyclic Peptides

The mix of 15 cyclic peptides given in Section 2 above ("Direct binding of anti-Id to the synthetic peptides") was used to inhibit the binding of anti-Id to anti-dsDNA antibodies affinity purified from each of 7 Lupus patients. The mixture was made to increase the recognition probability of the anti-dsDNA Id(s) of the Lupus patient.

ELISA plates were coated with anti-Fc 2 ug/ml in NaHCO3 0.05M pH 8.5 over night at 4° C. In this way the F(ab) portion of the immunoglobulin molecule of anti-dsDNA will present the idiotype more efficiently.

The plates were blocked with 3% BSA for 1 hr at 37° C., and each human anti-dsDNA antibody solution was added at 10 ug/ml in PBS, and incubated overnight at 4° C. In separate tubes peptide mix 1 was added at different concentrations to biotinylated anti-dsDNA anti-Id from IVIG (at a concentration of 50% binding to anti-dsDNA) for overnight incubation at 4° C. The day after, the mixture of anti-Id and peptide mix was added to the anti-dsDNA coated plates for 4 hrs. The binding of unbound anti-Id which was not recognized by the peptide mix was probed with streptavidine conjugated with alkaline phosphatase and an appropriate substrate.

The results presented in Table 4 show percentages of inhibition of IVIG specific fraction of anti-dsDNA anti-Id binding to anti-dsDNA from a particular Lupus patient by the peptide mixture.

TABLE 4

| μg/ml | Pat #1 | Pat #2 | Pat #3 | Pat #4 | Pat #5 | Pat #6 | Pat #7 |
|---|---|---|---|---|---|---|---|
| 2000 | 95.2 | 93.4 | 85.7 | 57.6 | 94.0 | 94.7 | 60.5 |
| 1000 | 92.2 | 91 | 74.3 | 12.8 | 90.1 | 92 | 34.6 |
| 500 | 87.4 | 94 | 49.1 | 5.3 | 85.4 | 81 | 12.6 |
| 250 | 45.3 | 69.1 | 23.5 | 2.8 | 51.3 | 56.4 | 5.4 |
| 125 | 21.2 | 32.4 | 11.7 | 1.1 | 27.1 | 21.7 | 1.9 |
| 620 | 9.3 | 12.9 | 2.6 | 0.6 | 11.5 | 11.7 | 0.6 |
| 31 | 4.3 | 5.3 | 1.1 | 0.9 | 4.3 | 4 | 0.2 |
| 15 | 3.8 | 2.1 | 0.7 | 0.3 | 2.1 | 0.1 | 0.4 |
| 7.5 | 4.1 | 1.9 | 0.4 | 0.5 | 1.6 | 3.3 | 0.5 |
| 3.25 | 2.3 | 0.6 | 0.2 | 0.2 | 1.1 | 1.1 | 0.1 |
| 1 | 2.1 | 0.3 | 0.3 | 0.1 | 0.6 | 0.7 | 0.2 |
| 0.5 | 1.9 | 0.7 | 0.6 | 0.1 | 0.5 | 0.6 | 0.1 |
| 0.25 | 0.6 | 0.1 | 0.1 | 0.1 | 0.2 | 0.5 | 0.1 |
| 0.1 | 0.5 | 0.1 | 0.5 | 0.1 | 0.1 | 0.1 | 0.4 |

Example IV

Using IVIG and/or Pooled Plasma as a Template for the Isolation of Idiotypic Mimicries of Autoimmune Disease 1. Introduction:

The present example provides an experimental demonstration of direct selection in the conventional way which resulted in the identification of the common SLE idiotype, Id 16/6. It has been proven that one of the peptides based on the 16.6 CDRs, CDR3, can cause SLE symptoms in mice, whereas CDR1's predominate function is to ameliorate the disease in experimental SLE mice (1).

Two peptides based on the sequences of the complementary-determining regions (CDR) of the pathogenic murine monoclonal anti-DNA Ab (5G12) that bears the 16/6 Id were synthesized. pCDR1 (CDR1-T GYYMQWVKQSPEKSLEWIG) and pCDR3 (CDR3-YY-CARFLWEPYAMDYWGQGS) (the CDRs are underlined) were shown to be immunodominant T-cell epitopes in BALB/c and SJL mouse strains, respectively, and induced a mild SLE-like disease in responder mice (Kent, S. B. H., Hood, L. E., Beilan, H., Meister, S. & Geiser, T. (1984) in *High Yield Chemical Synthesis of Biologically Active Peptides on an Automated Peptide Synthesizer of Novel Design*, ed. Ragnarsson, U. (Almqvist & Wiksell, Stockholm), pp. 185-188). Further, the CDR-based peptides inhibited the priming of lymph-node cells (LNC) of mice immunized with the same peptides or with the monoclonal anti-DNA 16/6Id+ Abs of either mouse or human origin. The CDR1-based peptide was also shown to prevent auto-Ab production in BALB/c neonatal mice that were immunized later with either pCDR1 or the pathogenic auto-Ab (Kent, op.cit.).

2. Materials and Method 2.1 Synthetic Peptides.

The 16.6 monoclonal antibody CDR1-based peptide T GYYMQWVKQSPEKSLEWIG (pCDR1), designated 706, and the CDR3-based peptide YYCAR FLWEPYAMDYWGQGS (pCDR3), designated 707, were prepared with an automated synthesizer (Applied Biosystem model 430A) using the company's protocols for t-butyloxycarbonyl (BOC) strategy (Kent, op.cit., Schnolzer, M., Alewood, P. F. & Kent, S. B. H. (1992) *Int. J. Pept. Protein Res.* 40, 180-193). The reverse order of CDR1 designated R706 GIWELSKEPSQKVWQMYYGT was used as a control. In another similar synthesis, the resulting peptides were labeled by biotin at their N-terminal, later to be used in the ELISA testing.

2.2 Affinity Chromatography: Preparation of the Peptide Column 2.2.1 Coupling of Peptide 707 by Reductive Amination 2.2.1.1 Activation Protocol a. Creation of Periodate-Oxidizable Matrix 10 ml of Toyopearl MH65F (Tosohass, Japan) were washed with 300 ml water on a sintered glass filter (porosity G3) followed by 5 successive (total 80 ml) washes with 1M NaOH. The resin was taken out of the sintered glass filter and suspended with 10 ml of 1M NaOH, 1 ml of glycidol (Sigma) and 0.01 g of Sodium Borohydrate (NaBH$_4$). The reaction mixture was incubated at room temperature overnight with gentle rolling. In the morning, the resin was washed extensively with 200 ml of each of water, 1M NaCl and again with water. The glycidol-modified resin was now ready for periodate oxidation.

b. Direct Periodate Oxidation of the Matrix

The following protocol was designed to prepare periodate oxidation resin: 10 ml wet gel containing vicinal hydroxyl groups were resuspended in 10 ml 0.2M NaIO4 (4.28 g of sodium meta-periodate in 100 ml of water) and mixed well by gentle rolling. The reaction was continued for 90 min. at room temperature. The formyl resin was washed by 300 ml of water to stop the oxidation. The aldehydes created by this procedure are stable enough to allow the resin to be stored for long periods without a decrease in coupling potential.

2.2.1.2 Ligand Coupling Protocol 1 ml of phosphate buffer, pH 7.0 containing NaCNBH$_4$ and the specific peptide was added to 2 ml of periodate-oxidized matrix. The concentration of the peptides in the phosphate buffer was 10 mg/ml (about 3.3 μmoles/ml). Therefore the ratio was 1.1 μmole of 707 to ml resin. The reaction continued with stirring overnight at room temp. The coupled resin was washed extensively with water, 1M NaCl and again with water to remove unreacted ligand and sodium cyanoborohydride.

The resin was stored in 20 Mm phosphate buffer pH 7.

2.2.2 Coupling of Peptide 706 to CNBr-Activated Matrix 3 g of freeze dried CNBr activated Sepharose 4 fast flow were suspended in 20 ml of 1 mM HCl (ice cold). The resin was washed intensely for 15 min. on a sintered glass filter (porosity G3) using 200 ml of acid. After the final wash, 2 ml of the washed resin were transferred to coupling solution, in which the peptide to be coupled had been dissolved. The coupling solution contained 900 μl of 0.1-M sodium carbonate (NaHCO$_3$), pH 8.5 and 1000 of 100 mg/ml of peptide 706. The ratio of peptide to resin was again 1.1 mole per ml of resin. The mixture was rolled overnight at 4° C. After coupling, the vial with the resin was left at a vertical position for sedimentation of the resin. The supernatant was discarded and 15 ml of 0.2M glycine, pH 8.0 were added for blocking of the remaining active groups on the resin. The blocking was performed at room temperature for 4.5 hours, while rolling.

After blocking, the resin was washed with 10 column volumes of 0.1 M sodium carbonate (NaHCO$_3$), pH 8.5 following by washing with 3 cycles of alternating pH. Each cycle consisted of a 15 ml wash of 0.1 M acetate buffer pH 4 containing 0.5 M NaCl followed by a wash with 0.1 M Tris HCl buffer pH 8 containing 0.5M NaCl.

The resin was stored in 0.05 M Tris pH 7.4

2.3 Affinity Chromatography: Purification of Anti-Idiotypes from an Intravenous Immunoglobulin Solution Using the Peptide Column.

The peptide columns were washed with at least 10 volumes of loading buffer (20 mM PB) until the absorbance measurement at 280 nm was stable (OD about 0.005).

100 ml of diluted IVIG (in process sample G-12 of the OmriGam, (Omrix Biopharmaceuticals Ltd, Israel) production process, high purified double inactivated IVIG) were loaded on top of a 2 ml peptide resin. The concentration of the starting material was 50 mg/ml. In order to reach this concentration, the IVIG was diluted with phosphate buffer, pH 7 to reach the desired molarity. The loading proceeded overnight at 4° C. at a flow rate of 100 μl/min, approximately. The loading was performed twice. The column was then washed with loading buffer until the absorbance at 280 reached baseline. The elution was done with 0.1M glycine, HCl pH 2.7 into 1M Tris base buffer pH 9 to neutralize the eluate. Each elution consisted of a peak, usually of about 4-5 ml from a 1 ml column. Protein in the elution and the loading was measured by the Bradford method (Bradford (1976) *Anal. Biochem.* 72:248).

2.4 Efficacy of the Affinity Chromatography Step: ELISA

To measure the binding efficacy of peptide column eluates (706 and 707) the following ELISA was performed:

Microtiter plates (Costar, USA) were coated overnight at 2-8° C. with 10 μg/ml NeutrAvidin (Pierce, USA) suspended in 0.1M, pH 8.8, of carbonate-bicarbonate buffer (Sigma USA). The coating solution was removed, washed three times with washing buffer (1×PBS) and 2000 of blocking solution (freshly prepared 1% I Block, Tropix, USA) per well was added and incubated for 1 hour at 37° C. Coated and blocked plates can be stored at −20° C. for a month before use.

Tested samples diluted in the blocking solution were mixed in a separate tube with 1 µg/ml (final concentration) of the appropriate biotinylated peptide and the mixture was incubated for 1 hour at 37° C. 100 µl from each reaction tube was then transferred to the blocked microtiter plate and incubated at 37° C. for ½ hour. A 100 µl of 1:5000 Alkaline Phosphatase conjugate goat anti human IgG (Heavy and light chain from Jackson, USA) diluted in the blocking buffer was applied into the microtiter well and incubated for 1 hour. The enzymatic activity of alkaline phosphatase is then revealed by an overnight incubation at room temperature with p-nitrophenyl phosphate substrate (Sigma USA). The measurement was done photometrically at 405 nm.

3. Results and Discussion.

200 ml of IVIG were loaded on each of the 2 ml peptide columns: one consisted of peptide 706 bind to a CNBr activated Sepharose matrix and the other a 707 peptide bind to the Polymeric matrix by reductive amination (see material and methods).

Figure 3:
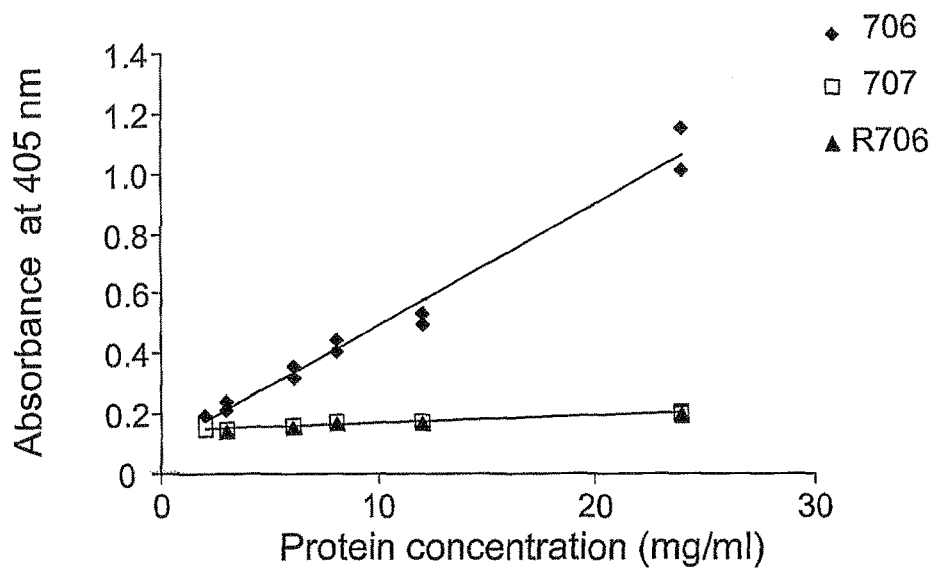
FIG. 3 is a graph illustrating specific binding of immunoglobulin peak elution to biotinylated peptides 706, 707 and R706 from a peptide column bearing the 706 peptide sequence.
Figure 4:
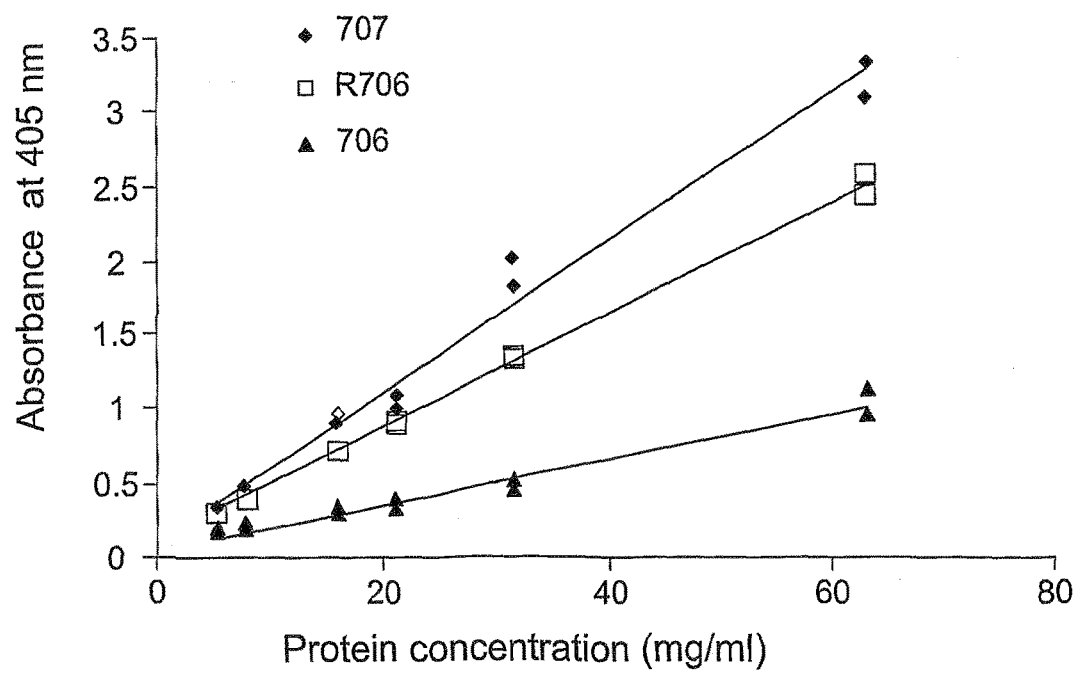
FIG. 4 is a graph illustrating specific binding of immunoglobulin peak elution to biotinylated peptides 706, 707 and R706 from a peptide column bearing the 707 peptide sequence.

The protein concentrations and the binding of biotinlyted peptides were tested, and the results are provided in table 5 and FIGS. 3 and 4.

TABLE 5

Protein yields of 200 ml of intravenous immunoglobulin (50 mg/ml) loaded on 2 ml peptide columns.

| Column used | Protein concentration in the elution (mg/ml) | Volume of the elution peak (ml) | Total protein in the elution peak (mg) | Protein recovery from load (%) |
|---|---|---|---|---|
| CNBr-706 | 0.60 | 3 | 1.80 | 0.018 |
| Reductive amination 707 | 1.58 | 3 | 4.74 | 0.047 |

The elution of the bound peak resulted in different recoveries: around 0.018% for column peptide 706 versus 0.047 for column peptide 707. Thus, it can be concluded that peptide column 706 has the capacity of binding one out of 5555 molecules whereas peptide column 707 has the capacity of binding one out of 2237 immunoglobulin molecules found in the pooled IVIG. It therefore could be assumed that the 707 epitope is more abundant and can be found at higher frequency in the IVIg.

The specificity of the elution peak was assessed by the specific binding to the peptide column elution peaks to three biotinylated peptides (706, 707 and R706) and the results are summarized in FIGS. 3 and 4.

It can be noted that immunoglobulin eluted from a peptide column bearing the peptide 706 reacted specifically in a linear fashion only with the biotinylated peptide of 706 and not with peptide 707 or even with a peptide bearing the same sequence in a reverse order (FIG. 3). On the other hand the elution peak from a peptide column bound with peptide 707 reacted in a non-specific manner (FIG. 4). The resulting immunoglobulin reacted with biotinylated peptide 706 and even more interesting the immunoglobulin reacted even more strongly with the reversed sequence of 706. Indicating that the 707-immunoglobulin preparations may react non-specifically with peptide sequences of 707 and 706 and probably with numerous other sequences.

The above results indicated that not all the CDR sequences found on the Id16.6 are specific and at least some of them react in a non specific manner with IVIg.

These results support the notion that the use of monoclonal derived from SLE patients may result in non-specific selection of immunoglobulin.

The invention claimed is:

1. A molecule which mimics an idiotype of an autoantibody, wherein the molecule consists of a peptide selected from the group consisting of:
   amino acid sequence KHETTET (SEQ ID NO:16),
   amino acid sequence AGLKNSQ (SEQ ID NO:18),
   amino acid sequence ASTIRAG (SEQ ID NO:19),
   amino acid sequence SQLGMVS (SEQ ID NO:23),
   amino acid sequence SASFTMI (SEQ ID NO: 30),
   amino acid sequence VGALPLE (SEQ ID NO:41),
   amino acid sequence TQEPSPL (SEQ ID NO:42),
   amino acid sequence PPNHSHL (SEQ ID NO:17),
   amino acid sequence PLSSSLP (SEQ ID NO:20),
   amino acid sequence SLQRHPW (SEQ ID NO:36),
   amino acid sequence FEVASLP (SEQ ID NO:37),
   amino acid sequence GDSLRST (SEQ ID NO:38),
   amino acid sequence NSRDSSE (SEQ ID NO: 39),
   amino acid sequence PLPDWRV (SEQ ID NO:40),
   amino acid sequence DWLYSRS (SEQ ID NO:43), and
   amino acid sequence LRVSTTE (SEQ ID NO:44),
   or a dimer, oligomer or polymer of said peptide.

2. A molecule according to claim 1 in the form of a dimer, oligomer or polymer of said peptide.

3. A composition comprising an effective amount of a molecule according to claim 1, together with a pharmaceutically acceptable excipient.

* * * * *

SEQUENCE LISTING

<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: synthetic

<400> SEQUENCE: 1

Arg Leu Thr Ser Ser Leu Arg Tyr Asn Pro
1               5                   10

<210> SEQ ID NO 2
<211> LENGTH: 30
<212> TYPE: PRT
<213> ORGANISM: Artificial Sequence
<220> FEATURE:
<223> OTHER INFORMATION: synthetic

<400> SEQUENCE: 2

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Thr Glu Lys Leu Arg Leu Arg Tyr Phe Asp Tyr Tyr Gly
1               5                   10

<210> SEQ ID NO 4
<211> LENGTH: 18
<212> TYPE: PRT
<213> ORGANISM: Artificial Sequence
<220> FEATURE:
<223> OTHER INFORMATION: synthetic

<400> SEQUENCE: 4

Leu Val Lys Pro Gly Gly Ser Leu Lys Leu Ser Cys Ala Ala Ser Gly
1               5                   10                  15

Phe Thr

<210> SEQ ID NO 5
<211> LENGTH: 16
<212> TYPE: PRT
<213> ORGANISM: Artificial Sequence
<220> FEATURE:
<223> OTHER INFORMATION: synthetic

<400> SEQUENCE: 5

Arg Leu Glu Trp Val Ala Thr Ile Ser Gly Asp Gly Gly Ser Tyr Thr
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: synthetic

<400> SEQUENCE: 6

Lys Gly Arg Phe Thr Ile Ser Arg Asp Asn Ala Lys Asn Thr Leu Tyr
1               5                   10                  15

Leu

<210> SEQ ID NO 7
<211> LENGTH: 12
<212> TYPE: PRT
<213> ORGANISM: Artificial Sequence
<220> FEATURE:
<223> OTHER INFORMATION: synthetic

<400> SEQUENCE: 7

Met Asn Trp Val Lys Gln Ser His Gly Lys Ser Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Phe Tyr Asn Gln Lys Phe Lys Gly Lys Ala Thr Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic

<400> SEQUENCE: 9

Ser Glu Asp Ser Ala Leu Tyr Tyr Cys Ala Arg Asp
1               5                   10

<210> SEQ ID NO 10
<211> LENGTH: 15
<212> TYPE: PRT
<213> ORGANISM: Artificial Sequence
<220> FEATURE:
<223> OTHER INFORMATION: synthetic

<400> SEQUENCE: 10

Tyr Tyr Tyr Gly Ala Gly Ser Tyr Tyr Lys Arg Gly Tyr Phe Asp
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(6)
<223> OTHER INFORMATION: CDR1

<400> SEQUENCE: 11

Thr Gly Tyr Tyr Met Gln Trp Val Lys Gln Ser Pro Glu Lys Ser Leu
1               5                   10                  15

Glu Trp Ile Gly
            20

<210> SEQ ID NO 12
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(15)
<223> OTHER INFORMATION: CDR3

<400> SEQUENCE: 12

Tyr Tyr Cys Ala Arg Phe Leu Trp Glu Pro Tyr Ala Met Asp Tyr Trp
1               5                   10                  15

Gly Gln Gly Ser
            20

<210> SEQ ID NO 13
<211> LENGTH: 20
<212> TYPE: PRT
<213> ORGANISM: Artificial Sequence
<220> FEATURE:
<223> OTHER INFORMATION: synthetic

```
<400> SEQUENCE: 13

Glu Ile Asn Pro Ser Thr Gly Gly Thr Thr Tyr Asn Gln Lys Phe Lys
1               5                   10                  15

Ala Lys Ala Thr
            20

<210> SEQ ID NO 14
<211> LENGTH: 19
<212> TYPE: PRT
<213> ORGANISM: Artificial Sequence
<220> FEATURE:
<223> OTHER INFORMATION: synthetic

<400> SEQUENCE: 14

Gly Tyr Asn Met Asn Trp Val Lys Gln Ser His Gly Lys Ser Leu Glu
1               5                   10                  15

Trp Ile Gly

<210> SEQ ID NO 15
<211> LENGTH: 17
<212> TYPE: PRT
<213> ORGANISM: Artificial Sequence
<220> FEATURE:
<223> OTHER INFORMATION: synthetic

<400> SEQUENCE: 15

Tyr Tyr Cys Ala Arg Ser Gly Arg Tyr Gly Asn Tyr Trp Gly Gln Thr
1               5                   10                  15

Leu

<210> SEQ ID NO 16
<211> LENGTH: 7
<212> TYPE: PRT
<213> ORGANISM: Artificial Sequence
<220> FEATURE:
<223> OTHER INFORMATION: synthetic

<400> SEQUENCE: 16

Lys His Glu Thr Thr Glu Thr
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic

<400> SEQUENCE: 17

Pro Pro Asn His Ser His Leu
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic

<400> SEQUENCE: 18

Ala Gly Leu Lys Asn Ser Gln
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: synthetic

<400> SEQUENCE: 19

Ala Ser Thr Ile Arg Ala Gly
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic

<400> SEQUENCE: 20

Pro Leu Ser Ser Ser Leu Pro
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic

<400> SEQUENCE: 21

Phe Leu Thr Leu Thr Glu Leu
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic

<400> SEQUENCE: 22

Val Arg Val Leu Leu Arg Ser
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic

<400> SEQUENCE: 23

Ser Gln Leu Gly Met Val Ser
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic

<400> SEQUENCE: 24

Ser Glu His Thr Thr Val His
1               5

<210> SEQ ID NO 25
```

```
<211> LENGTH: 7
<212> TYPE: PRT
<213> ORGANISM: Artificial Sequence
<220> FEATURE:
<223> OTHER INFORMATION: synthetic

<400> SEQUENCE: 25

Thr Gln Pro Pro Glu Leu Pro
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic

<400> SEQUENCE: 26

Leu Ser Gln Pro Glu Arg Trp
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic

<400> SEQUENCE: 27

Pro Pro Pro Asp Leu His Ala
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic

<400> SEQUENCE: 28

Glu Glu Ser Ser Tyr Leu Val
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic

<400> SEQUENCE: 29

Ser Asn Glu Gln Met Leu Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic

<400> SEQUENCE: 30

Ser Ala Ser Phe Thr Met Ile
1               5

<210> SEQ ID NO 31
<211> LENGTH: 7
```

```
<212> TYPE: PRT
<213> ORGANISM: Artificial Sequence
<220> FEATURE:
<223> OTHER INFORMATION: synthetic

<400> SEQUENCE: 31

Gly Thr Thr Gln Trp Val Leu
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic

<400> SEQUENCE: 32

His Ser Leu Thr Gln Pro Ala
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic

<400> SEQUENCE: 33

Gln Leu Ala Leu His Ser Thr
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic

<400> SEQUENCE: 34

Tyr Gly Thr Pro Ser Ser Glu
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic

<400> SEQUENCE: 35

Lys Met His Ser Val Gly Ser
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic

<400> SEQUENCE: 36

Ser Leu Gln Arg His Pro Trp
1               5

<210> SEQ ID NO 37
<211> LENGTH: 7
<212> TYPE: PRT
```

```
<213> ORGANISM: Artificial Sequence
<220> FEATURE:
<223> OTHER INFORMATION: synthetic

<400> SEQUENCE: 37

Phe Glu Val Ala Ser Leu Pro
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Gly Asp Ser Leu Arg Ser Thr
1               5

<210> SEQ ID NO 39
<211> LENGTH: 7
<212> TYPE: PRT
<213> ORGANISM: Artificial Sequence
<220> FEATURE:
<223> OTHER INFORMATION: synthetic

<400> SEQUENCE: 39

Asn Ser Arg Asp Ser Ser Glu
1               5

<210> SEQ ID NO 40
<211> LENGTH: 7
<212> TYPE: PRT
<213> ORGANISM: Artificial Sequence
<220> FEATURE:
<223> OTHER INFORMATION: synthetic

<400> SEQUENCE: 40

Pro Leu Pro Asp Trp Arg Val
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic

<400> SEQUENCE: 41

Val Gly Ala Leu Pro Leu Glu
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic

<400> SEQUENCE: 42

Thr Gln Glu Pro Ser Pro Leu
1               5

<210> SEQ ID NO 43
<211> LENGTH: 7
<212> TYPE: PRT
<213> ORGANISM: Artificial Sequence
```

```
<220> FEATURE:
<223> OTHER INFORMATION: synthetic

<400> SEQUENCE: 43

Asp Trp Leu Tyr Ser Arg Ser
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic

<400> SEQUENCE: 44

Leu Arg Val Ser Thr Thr Glu
1               5

<210> SEQ ID NO 45
<211> LENGTH: 7
<212> TYPE: PRT
<213> ORGANISM: Artificial Sequence
<220> FEATURE:
<223> OTHER INFORMATION: synthetic

<400> SEQUENCE: 45

Pro Pro Gln Lys His Leu Leu
1               5

<210> SEQ ID NO 46
<211> LENGTH: 7
<212> TYPE: PRT
<213> ORGANISM: Artificial Sequence
<220> FEATURE:
<223> OTHER INFORMATION: synthetic

<400> SEQUENCE: 46

Glu Met Thr Ala Thr Val Ser
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic

<400> SEQUENCE: 47

Val Arg Leu Glu Gly Leu Pro
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic

<400> SEQUENCE: 48

Lys Tyr Lys Arg Lys Tyr Pro
1               5

<210> SEQ ID NO 49
<211> LENGTH: 20
<212> TYPE: PRT
<213> ORGANISM: Artificial Sequence
<220> FEATURE:
```

<223> OTHER INFORMATION: synthetic

<400> SEQUENCE: 49

Gly Ile Trp Glu Leu Ser Lys Glu Pro Ser Gln Lys Val Trp Gln Met
1               5                   10                  15

Tyr Tyr Gly Thr
            20